(12) United States Patent
Silverglate et al.

(10) Patent No.: US 6,597,457 B1
(45) Date of Patent: Jul. 22, 2003

(54) CALIBRATION OF SOLAR REFLECTANCE PANEL

(75) Inventors: Peter R. Silverglate, Monroe; Richard A. Rockwell; Edward F. Zalewski, both of Sandy Hook, all of CT (US)

(73) Assignee: Goodrich Corporation, Charlotte, NC (US)

( * ) Notice: Subject to any disclaimer, the term of this patent is extended or adjusted under 35 U.S.C. 154(b) by 0 days.

(21) Appl. No.: 09/960,106

(22) Filed: Jan. 6, 1994

Related U.S. Application Data

(63) Continuation of application No. 07/804,321, filed on Dec. 9, 1991, now abandoned.

(51) Int. Cl.[7] .............................................. G01N 21/47
(52) U.S. Cl. ...................................... 356/446; 356/236
(58) Field of Search ................................ 356/236, 445, 356/446, 447, 448; 250/228

(56) References Cited

U.S. PATENT DOCUMENTS

| | | | | |
|---|---|---|---|---|
| 3,432,243 A | * | 3/1969 | Hardesty | 250/228 |
| 4,310,246 A | * | 1/1982 | Blazek | 356/236 |
| 4,444,499 A | * | 4/1984 | Akiyama et al. | 356/448 |
| 4,746,214 A | * | 5/1988 | Akiyama et al. | 356/236 |
| 4,770,530 A | * | 9/1988 | Van Aken et al. | 356/448 |
| 4,932,779 A | * | 6/1990 | Keane | 356/236 |
| 5,231,461 A | * | 7/1993 | Silvergate et al. | 356/326 |

* cited by examiner

Primary Examiner—Richard A. Rosenberger

(57) ABSTRACT

Calibration is provided for a diffuser panel (30) on board a spacecraft (10) employed in measuring the intensity of sunlight reflected from subjects on the earth. The calibration is accomplished by comparing the intensity of solar radiation reflected from the panel with the intensity of the solar radiation incident directly from the sun. The comparison is obtained by directing both radiation into an integrating sphere (60) through separate ports (62, 64) which are sized to admit substantially equal amounts of power of the reflected and the direct radiations. A detector (76) detects an average value of intensity of the reflected radiation while the direct rays are excluded by a shutter (94). Upon an opening of the shutter and a deflecting of the diffuser panel from the calibrating position, the detector detects the average value of radiation intensity from the direct rays of the sun. The detected values of the radiation intensities may be transmitted back to earth, or are stored in memories 108 and 110 of a computer 100, and then applied to an arithmetic unit 114 to produce the calibration ratio which is then made available for transmission with imaging data back to the earth.

18 Claims, 2 Drawing Sheets

CALIBRATION OF SOLAR REFLECTANCE PANEL

This is a continuation of application Ser. No. 07/804,321 filed Dec. 9, 1991 now abandoned.

BACKGROUND OF THE INVENTION

This invention relates to use of a solar irradiance diffuser panel for measurements from a spacecraft of solar radiation reflected from earth and, more particularly, to a method and apparatus for in-flight calibration of the diffuser panel.

There is interest in the measurement of solar light or radiation reflected from the earth. Apparatus for performing the measurement is carried by a spacecraft. It is convenient to state the measurement of the reflected light in terms of a percentage of the intensity of sunlight incident upon the earth. One way of establishing the percentage reflection is to employ a solar irradiance diffuser panel to reflect incident solar radiation to the measurement apparatus. Thereby, the diffuser panel serves as a diffuse reference source of solar radiation in the measurement process. The measurement apparatus measures the intensity of the reference source, namely, the light reflected from the diffuser panel, and also measures the intensity of light reflected directly from the earth. By comparing the two measurements, the measurement of the intensity of the reflected light from the earth is expressed readily as a fraction or percentage of the intensity of the incident solar radiation as represented by the reflectance of the reference diffuser. Data of the reflected light is transmitted back to a receiving station on the earth.

A problem arises in that the spectral reflectance characteristics of the diffuser panel may change with time on board the spacecraft. Since the diffuser panel is employed in the reference source, any change in the reflectance characteristic distorts the data transmitted back to earth.

A further problem is that, in addition to direct sunlight on the diffuser panel, some light may be scattered from the spacecraft or other instruments on board the spacecraft. The diffuser will then have a higher reflected radiance output which will be interpreted as erroneously low reflectances of earth scenes.

SUMMARY OF THE INVENTION

The aforementioned problems are overcome and other advantages are provided by the invention which enables a calibration of the diffuser panel on board the spacecraft as the spacecraft orbits the earth. This is accomplished by comparing intensity of solar radiation (direct and scattered) reflected from the panel with the intensity of the solar radiation (direct only) incident from the sun. The two measurements allow the solar reflectance of the panel to be expressed as a percentage of the incident solar radiation intensity. The ratio, which may be referred to as the calibration ratio, serves as a measure of the panel reflectance. The calibration of the panel is performed when the diffuser panel first enters service as the reference source, and at later times to develop a history of the calibration ratio. The calibration ratio, or data for calculation of the calibration ratio, is transmitted back to earth with the measurement of the earth's reflected light for correction of the reflectance measurement, thereby to compensate for drift in the diffuser panel characteristics.

The invention is carried out by use of a radiation averaging chamber which may be constructed in spherical shape, and is provided with a diffuse inner reflecting surface to induce multiple reflection of radiation to accomplish an averaging of the radiation. Two ports are provided in a wall of the chamber for entry of radiation, a first of the ports being employed for viewing solar radiation reflected by the diffuser panel, and the second of the ports being employed for sighting solar radiation propagating directly from the sun to the second port. It is advantageous to provide an assembly of baffles encircling the first port to limit the viewing of incoming radiation to only those rays of radiation reflected from the diffuser panel, thereby to exclude any interfering radiation which may be reflected off of other portions of a spacecraft carrying the averaging chamber or from other equipment carried by the spacecraft. Similarly, it is advantageous to encircle the second port with a tubular structure which is pointed towards the sun for receiving only those rays propagating directly from the sun while excluding rays of radiation which may reflect from the spacecraft or equipment carried by the spacecraft from entering the second port.

At least one detector of radiation, such as a photodetector, is located outside the averaging chamber and is optically coupled via a third port to the interior of the chamber for detection of radiation therein. If desired, a lens, such as a fisheye lens may be employed at the third port to facilitate a gathering of radiation to be detected by the detector. Also, if desired, a filter may be located between the lens and the detector to limit radiation incident upon the detector to radiation within a specific portion of the electromagnetic spectrum established by a passband of the filter. Furthermore, if desired, instead of the single photodetector, plural photodetectors each with a different filter may be located at separate ports to detect spectrally different changes in the diffuser reflectance. It is also advantageous to provide shutters at one or both ports for excluding light from the sun during a viewing of radiation from the diffuser panel, or for excluding light from the diffuser panel during a sighting of radiation from the sun.

The foregoing apparatus is employed for calibrating the diffuser panel by sighting the sun via the second port, and detecting the intensity of radiation within the averaging chamber by use of the detector. In the preferred embodiment of the invention, two shutters are employed, namely, a panel shutter positioned in the first port by which the diffuser panel is viewed, and a sun shutter positioned in the second port which serves for sighting the sun. Thereupon, the sun shutter is closed, and the panel shutter is opened to enable the first port to view radiation, which may be light in the visible, ultraviolet and/or infrared portions of the spectrum, reflected from the diffuser panel. The viewing is accomplished by use of the detector(s) each of which detects the intensity of radiation inside the averaging chamber provided by the diffuser panel. Electronic circuitry connected to the detector(s) provides for storing the values of detected radiation. Thereupon, the radiation detected during the viewing of the diffuser panel is divided by the value of radiation detected during the sighting of the sun to obtain a ratio which is useful in calibrating the diffuser panel. An initial value of the calibration ratio is obtained when the diffuser panel is first put into service. Subsequent values of the calibration ratio indicate the presence of a drift in the reflected characteristics of the diffuser panel, or a change in the characteristics of the scattered light. The calibration ratios (or data for calculation of the ratio as will be explained hereinafter) are transmitted along with data of the earth's reflected light back to a receiving station on the earth. In this way, drift data of the diffuser panel and scattered light changes, in the form of updated values of the calibration ratio can be used to compensate for any drift which may be present in the reflectance characteristics of the diffuser panel, or in the light scattered from the space craft. The compensated values of the diffuser panel reflectances can then be used in correcting the measured values of light reflectances from the earth.

It is advantageous in the use of the averaging chamber to select an aperture size for the second (sun) port which is smaller than the aperture of the first (panel) port, thereby to equalize substantially the amount of radiation power entering the averaging chamber directly from the sun via the second port with the radiant power entering the averaging chamber from the diffuser panel via the first port. This reduces the requisite dynamic range of the detector so as to provide for a more accurate establishment of the calibration ratio.

BRIEF DESCRIPTION OF THE DRAWING

The aforementioned aspects and other features of the invention are explained in the following description, taken in connection with the accompanying drawing wherein.

DETAILED DESCRIPTION

Figure 1:
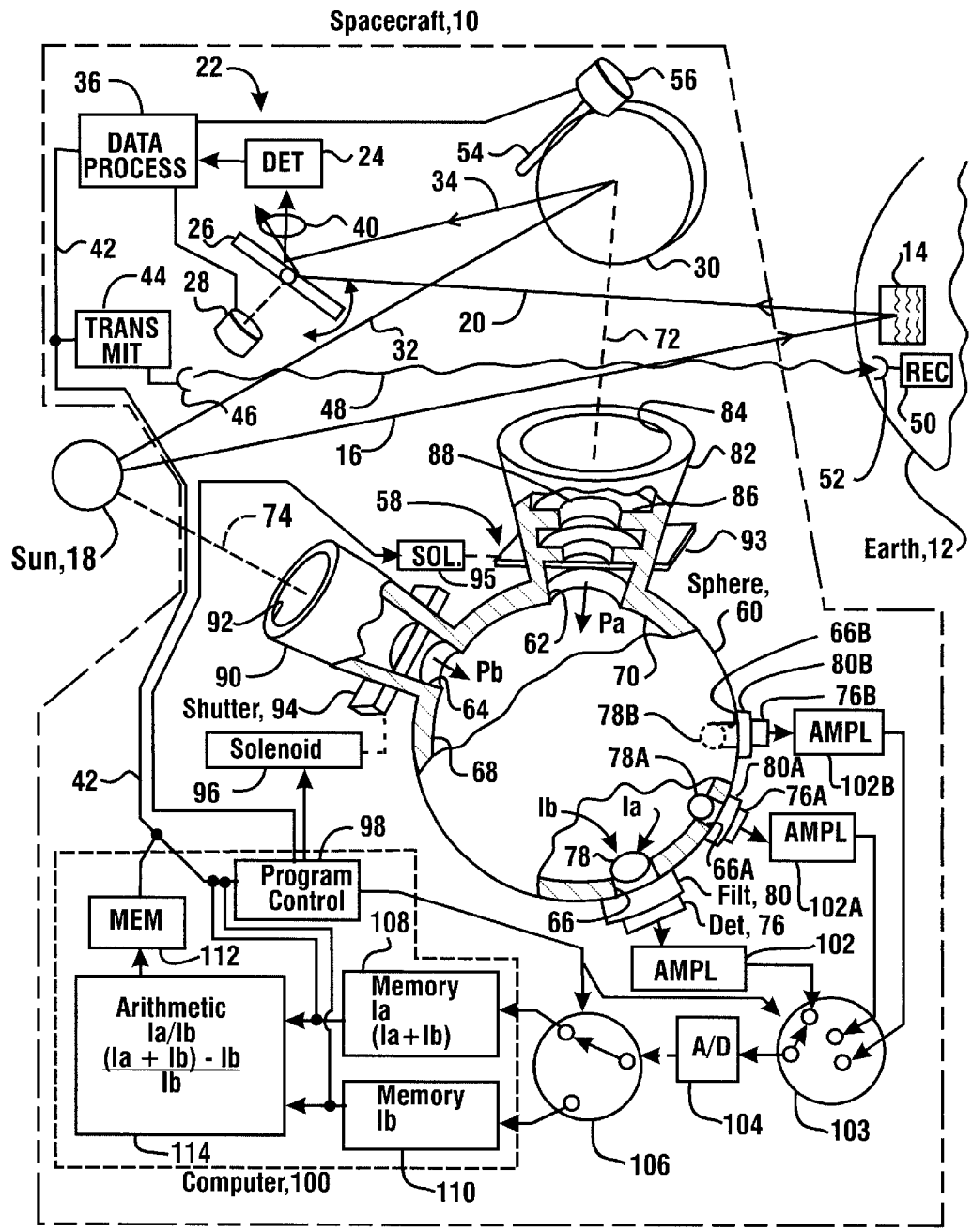
FIG. 1 shows, diagrammatically and in a stylized view, optical calibrating apparatus including an averaging chamber and a plurality of ports, in accordance with the invention, for viewing light from a diffuser panel and light from a reference source employing the sun.

The figure shows a spacecraft 10 encircling the earth 12 for obtaining imaging data of a subject 14 wherein the subject 14 may be, by way of example, a farm growing crops. The subject 14 is illuminated with rays 16 of radiation from the sun, and at least a portion of the incident radiation is reflected by the subject 14 as reflected rays 20 which propagate towards the spacecraft 10. The spacecraft 10 carries imaging equipment 22 which includes a detector assembly 24 and a tilting mirror 26. The mirror 26 is positioned by a motor 28 to reflect the rays 20 to the detector assembly 24.

In the use of the imaging equipment 22, it is important to provide a measure of the intensity of the rays 20 reflected from the subject 14. In order to establish a basis for measuring the intensity of the rays 20, a standard reference source of light is provided to serve as a basis for comparison of the intensity of the rays 20. The standard reference source of light is obtained by use of a solar irradiance diffuser panel which is illuminated with radiation from the sun 18 via rays 32, and reflects the radiation via rays 34 to the mirror 26. The mirror 26 may be tilted in either of two positions, namely, a first position for reflecting the rays 20 of the subject 14 to the detector assembly 24, and a second position for reflecting the rays 34 of the panel 30 to the detector assembly 24. Output signals of the detector assembly 24 are applied to a data processor 36 of the imaging equipment 22 which compares the intensities of the radiations reflected from the subject 14 and from the panel 30 to establish the value of intensity of the subject radiation. For example, the subject radiation may be equal to one-half or one-quarter of the intensity of the radiation reflected by the panel 30. In this way, the sunlight from the sun 18 is used to illuminate the subject 14 as well as to provide the standard reference source of light against which reflected radiance of the subject 14 is to be judged.

The data processor 36 includes well-known circuitry (not shown) for activating the motor 28 to tilt the mirror 26 between its two positions so as to provide solar radiation data, alternately, from the subject 14 and from the diffuser panel 30 to the detector assembly 24. Also included within the imaging equipment 22 is a lens 40 which serves to focus either of the rays 20 and 34 upon the detector assembly 24 via optical paths which are folded by the mirror 26. If desired, colored filters (not shown) may be included with the lens 40 for measuring specific portions of the solar spectrum, such as the intensity of green light or red light, by way of example. Data of the reflected radiance of the subject 14 is outputted by the data processor 36 in digital format upon a data bus 42 for transmission back to the earth 12 via a transmitter 44 and antenna 46 which are carried by the spacecraft 10. The data propagates from the antenna 46 as an r.f. (radio frequency) signal link 48 to be received at a receiving station 50 via an antenna 52 on the earth 12. The diffuser panel 30 is supported by an arm 54 rotatable by a motor 56. The data processor 36 includes suitable drive circuitry (not shown) for operating the motor 56 to position the diffuser panel 30 for reflecting sunlight via the lens 40 and the mirror 26 to the detector assembly 24.

In accordance with the invention, the spacecraft 10 also carries calibration equipment 58 for calibrating the reflectance of the diffuser panel 30. The panel 30 may be constructed of a plastic material such as a fluorocarbon, and may be provided with a surface comprising microspheres of the fluorocarbon material, to provide for diffuse reflection of incident light with no more than a negligible loss of radiant energy in the reflection process. Other panel coatings, such as roughened aluminum or a diffusely reflecting paint, may also serve as a reflecting surface. However, continuous intense illumination of the panel by intense sunlight, as well as other factors such as a possible aging or the presence of interstellar dust, may cause deterioration of the light-reflective capacity of the panel 30. In order to ensure an accurate measurement of the intensity of radiation reflected from the subject 14, the invention provides for the transmission, via the r.f. signal link 48, of additional data indicating the light-reflective capacity of the panel 30 so as to permit correction of the imaging data to compensate for any drift in the light-reflective capacity of the panel 30.

The calibration equipment 58 comprises a light, or radiation, averaging chamber constructed in the form of a sphere 60 with three ports 62, 64, and 66 providing passage for optical signals through a wall 68 of the sphere 60. An interior surface of the wall 68 is constructed as a diffusely reflecting surface 70 to provide for multiple reflection of radiation entering the sphere 60 via either of the ports 62 and 64, thereby to provide an average uniform intensity of the radiation within the sphere 60. The first port 62 is positioned for viewing solar radiation reflected by the panel 30 along a path 72. The second port 64 is positioned for viewing solar radiation directly from the sun 18 along a path 74. The third port 66 is provided with a detector 76, such as a photodetector, which views the radiation, or sunlight, within the sphere 60 for detecting the intensity of the radiation. If desired, in order to increase the strength of the optical signal incident upon the detector 76, a fisheye lens 78 may be employed at the port 66 for gathering rays of the radiation from a wide angle of view for refracting the rays to appear upon a front surface of the detector 76. Also, if desired, a colored filter 80 may be employed between the lens 78 and the filter 76 to select a specific portion of the electromagnetic spectrum, such as the yellow or blue light of the visible portion of the spectrum.

The colored filter 80 increases the accuracy of the measurement of the solar reflectance from the panel 30 by limiting the measurement to a specific region of the spectrum. Since it is possible for changes in the reflectance to occur as a function of frequency of the solar radiation, it is advantageous to provide additional filters covering different portions of the spectrum, two such filters 80A and 80B being shown by way of example in conjunction with additional detectors 76A and 76B and lenses 78A and 78B positioned, respectively, at a fourth port 66A and a fifth port 66B in the sphere 60. The operations of the additional filters 80A–B, the additional detectors 76A–B, and the additional lenses 78A–B are the same as those described for the filter 80, the detector 76 and the lens 78. By way of further example, the three filters 80, 80A and 80B may be colored red, yellow and blue, respectively. Suppose a contamination of the panel 30 introduces a yellowish discoloration. The detector 76A continues to output its signal obtained via the yellow filter 80A. However, the output signals of the other detectors 76 and 76B drop because of the reduction in the amount of reflected red and blue light. This arrangement of the multiple detectors with the differently colored filters, therefore, provides a more detailed assessment of the condition of the panel 30 to allow for correction of the various color components of an image.

The ports 62 and 64 are provided with shutter mechanisms, and with physical structures which limit the viewing angles of incident radiation as follows. The first port 62 is formed as a circular aperture in the wall 68 and further comprises a protruding tubular structure 82 having an outer wall 84 of cylindrical or frustoconical form, with a set of baffles 86 extending inwardly from the wall 84. The baffles 86 limit the view of radiation along the path 72 to light coming from the panel 30 while excluding light reflected from structural members (not shown) of the spacecraft 10 or equipment carried by the spacecraft 10. Each of the baffles 86, as shown in FIG. 1, is constructed of a circular disc with a central circular aperture 88 through which light passes to enter the sphere 60.

The second port 64 is formed as a circular aperture in the wall 68 and further comprises a tubular structure 90 comprising a wall 92 which may have a cylindrical or frustoconical shape. Both of the ports 62 and 64 are provided with shutters 93 and 94, respectively, which are movable by solenoids 95 and 96, respectively, to open or to close the respective ports 62 and 64 to the passage of radiation from the diffuser panel 30 and the sun 18. The solenoids 95 and 96 are activated electrically by a controller 98 of a computer 100. In the second port 64, a central bore of the tubular structure 90 is sufficiently narrow to exclude light reflected from structural components of the spacecraft 10 and from equipment mounted on the spacecraft 10, thereby to ensure that only light from the sun 18 enters the sphere 60.

The computer 100 is coupled to the detector 76 by means of an amplifier 102 connected to an output terminal of the detector 76, a switch 103, a converter 104 of electrical signals from analog to digital format, and a switch 106. The converter 104 is connected to the computer 100 by the switch 106, and to the amplifier 102 by the switch 103. Output terminals of the detectors 76A–B are connected similarly by amplifiers 102A–B to the switch 103, and by the switch 103 to the converter 104. The computer 100 includes three memories 108, 110, and 112, and an arithmetic unit 114. The switch 106 is operated by electric signals from the controller 98 to connect an output terminal of the converter 104 to an input terminal of either the memory 108 or the memory 110. The switch 103 is operated by electric signals from the controller 98 to connect an input terminal of the converter 104 to an output terminal of either of the amplifiers 102, 102A or 102B. The detectors 76, 76A and 76B detect incoming optical signals and convert the optical signals to electric signals which are outputted to the amplifiers 102, 102A and 102B, respectively. Each of the amplifiers 102, 102A and 102B amplifies the detector signals and may include a band-pass or low-pass filter (not shown) for reduction of noise which may accompany the signal. The signal outputted by each of the amplifiers 102, 102A and 102B has an analog format which is converted by the converter 104 to digital format and, then, is applied via the switch 106 to one of the memories 108 and 110.

In the operation of the calibration equipment 58, the controller 98 includes a program memory and address generator such as an address counter (not shown) for operating the computer 100 and providing other functions as will be described hereinafter. Even though the diffuser panel 30 is directing solar radiation toward the mirror 26, the diffuse reflection characteristic is sufficiently uniform to reflect enough radiation in the direction of the port 62 to allow for a measurement of the panel reflectance by the detector 76. During a viewing of the panel 30 via the port 62, the controller 98 directs the solenoid 96 to close the shutter 94 to exclude the direct passage of sunlight along the path 74 into the sphere 60. Thus, sunlight is entering the sphere 60 only via the path 72 to input radiant power, Pa, into the sphere 60. The controller 98 directs the switch 106 to couple signals from the converter 104 to the memory 108. The radiant power, Pa, radiates throughout the interior of the sphere 60 by diffuse multiple reflections of the radiation to produce an average radiation intensity, Ia, which is detected by the detectors 76, 76A and 76B and stored in the memory 108. Operation of the switch 103 allows sampling of each of the output signals of the respective detectors 76, 76A and 76B for transmission of these signals to the computer 100.

Thereafter, the controller 98 directs the solenoid 95 to close the shutter 93, after which the controller 98 directs the solenoid 96 to open the shutter 94 to allow sunlight to propagate along the path 74 directly from the sun 18 into the sphere 60 to provide radiant power, Pb, into the sphere 60. The radiant power, Pb, is distributed uniformly about the interior of the sphere 60 by multiple diffuse reflections from the interior reflecting surface 70 to produce an average value of radiation intensity, Ib. The controller 98 directs the switch 106 to couple the converter 104 to the memory 110. The value of the radiation intensity, Ib, is detected by the detectors 76, 76A and 76B and is stored in the memory 110.

The contents of the memories 108 and 110 are applied to the arithmetic unit 114 which computes the ratio of the panel intensity, Ia, divided by the direct solar intensity, Ib. This ratio is stored in the memory 112 for subsequent transmission via the data bus 42 and the r.f. signal link 48 to the receiving station 50 along with imaging data provided by the imaging equipment 22. The ratio of the intensities is established initially, at each spectral portion established by respective ones of the filters 80, 80A and 80B, when the panel 30 is first brought into service, and at subsequent times throughout the life of the imaging equipment 22. Variations in the value of the intensity ratio provide personnel at the receiving station 50 with information as to the reflective capacity of the panel 30, and enable the personnel to correct for erroneous values of intensity of the subject radiation. For example, to consider an extreme case of the reflective capacity dropping by a factor of one-half, the apparent amplitude of the subject radiation would appear to be doubled. Upon normalizing the intensity ratios to make the initial ratio equal to unity, the subject radiation measurement is corrected by multiplying the radiation by the normalized intensity ratio, this having a value of one-half, to correct the radiation measurement.

It is possible to operate the calibration equipment 58 without the shutters 93 and/or 94 in the case wherein either the shutter 93 or 94 is jammed in the open position. The sun can be viewed separately from the diffuser panel 30 when the diffuser panel 30 is not deployed. This provides a sun-only signal. Radiation obtained by viewing only the diffuser panel 30 may be referred to as a panel-only signal. When the panel 30 is deployed and the panel plus the sun are viewed simultaneously, there results a combination-signal. The combination-signal can be adjusted to equal that of the panel-only signal by subtracting the previously measured sun-only signal. This is indicated by the mathematical notations in the blocks of the computer 100 in FIG. 1. Alternatively, baffling of the second (sun) port 64 may admit the direct solar radiation during a time which is brief compared to the time in which the diffuser panel 30 is irradiated by the sun. In this case, the panel-only signal is subtracted from the combination-signal to yield the sun-only signal. The inclusion of the shutters 93 and 94 serves to minimize contamination of the sphere interior as well as facilitating the calibration of the diffuser panel 30. Thus, with or without the shutters 93 and 94, the calibration equipment 58 provides the calibration ratio for compensation of the measurement of the subject radiation to account for changes in the reflective capacity of the diffuser panel 30.

A feature of the invention is the construction of the aperture of the first port 62 with a substantially larger diameter than the diameter of the aperture of the second port 64 so as to substantially equalize the values of the two power inputs Pa and Pb applied, respectively, to the sphere 60. This ensures that the levels of the averaged radiation intensities, respectively, Ia and Ib are substantially equal. Thereby, the detector 76 need operate over only a relatively small dynamic range, for maximum linearity and accuracy in the relative measurements of the intensity of the sunlight reflecting off the panel 30 and of the sunlight incident directly into the sphere 60.

Figure 2:
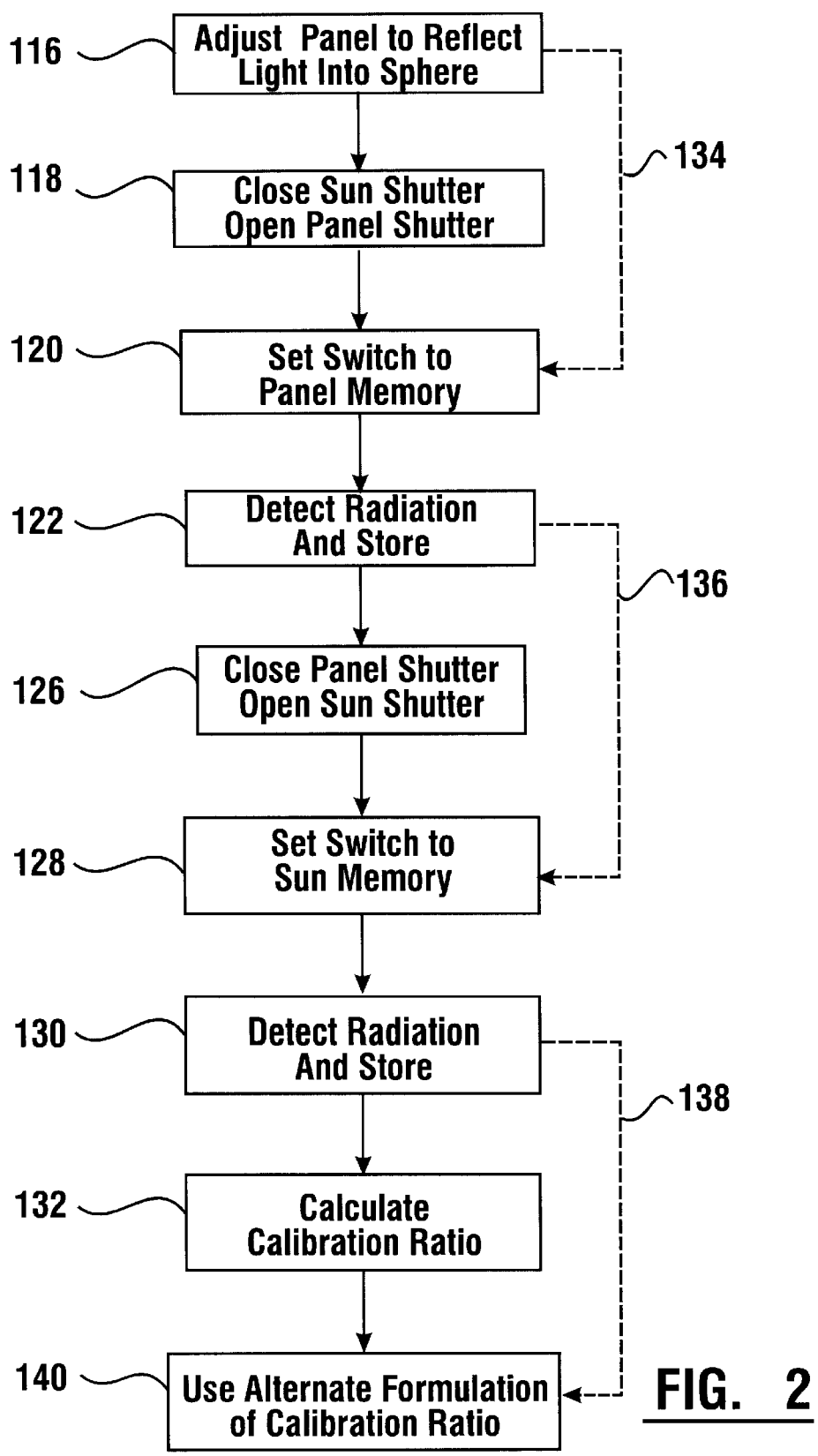
FIG. 2 shows a sequence of steps performed by calibration equipment of FIG. 1 to develop a calibration ratio for reflective capacity of a diffuser panel on board a spacecraft of FIG. 1.

FIG. 2 shows a flow chart for the foregoing steps of the controller 98 and the computer 100 for carrying out the calibration procedure to derive the calibration ratio for reflective capacity of the diffuser panel 30. The process begins at block 116 for adjusting the panel to reflect sunlight into the sphere. Then, in block 118, the solenoid 96 is activated to close the sun shutter 94, and the solenoid 95 is activated to open the diffuser-panel shutter 93. This is followed, at block 120, with a setting of the switch 106 to direct data from the converter 104 into the memory 108 for storing radiation data of the light reflected from the panel 30. Then, at block 122, a sample of the radiation detected by an individual one of the detectors 76, 76A and 76B is read into the memory 108. Then, at block 126, the panel shutter 93 is closed, and the sun shutter 94 is opened. At block 128, the switch 106 is set to couple radiation data of the direct sun illumination from the converter 104 into the memory 110. This is followed, at block 130, by the detection of a radiation sample of the sun's direct rays by the detector 76, and a feeding of the sample via the converter 104 to the memory 110. If desired, the order of the steps can be interchanged to allow for a sighting of the sun 18 via the second port 64, followed by a viewing of the diffuser panel 30 via the first port 62.

The computer 100 now has all the data necessary to calculate the calibration ratio and, accordingly, at block 132, the data is fed from the memories 108 and 110 into the arithmetic unit 114 to calculate the ratio of the two radiation intensities. The calibration ratio is then ready to be stored in the memory 112 for subsequent transmission via the data bus 42 and the r.f. signal link 48 to the receiving station 50. In the event that the shutter 94 is jammed in the open position, or in the event that the calibration equipment 58 is fabricated without the shutter 94, then the steps of the process proceed via the dashed lines 134, 136, and 138. This alternate procedure bypasses the shutter operation steps of blocks 118 and 126, and also replaces the calibration step of block 132 with that of block 140 for use of the alternate formulation of calibration ratio which is shown by the mathematical formula in FIG. 1, within the block of the arithmetic unit 114. As shown by the mathematical formulation, in the numerator of the fraction there is the subtraction of the intensity Ib from the sum of the intensities Ia plus Ib prior to implementing the division step.

In the use of spacecraft for gathering imaging data, it is a practice to transmit raw data to the receiving station 36 (FIG. 1) on the earth. This can be accomplished, as shown in FIG. 1, by outputting data from the memories 108 and 110 directly via the data bus 42 to the transmitter 44 for transmission via the antenna 46 to the receiving station 50. Also, with all of the raw data provided to the receiving station 36, if desired, the memory 112 plus the arithmetic unit 114 may be located at the receiving station 50 for performing the foregoing mathematical operations for the filter correction ratios, instead of in the spacecraft 10. For practicing the invention, these mathematical operations may be performed either in the spacecraft 10 or at the receiving station 50.

Thereby, the foregoing description has presented the capacity of the invention for calibrating the diffuser panel by use of sunlight as the reference source as the spacecraft orbits the earth. The invention enables accurate in-flight monitoring and correction of the reflectance calibration of a solar irradiance diffuser panel on board a spacecraft by a direct comparison of the panel's reflected solar radiance to the sun's irradiance. With the exception of the optional shutters, the calibration equipment employs no moving parts, and does not employ separate optical systems for the averaging and detection of the reflected radiation and direct radiation from the sun. The single optical system assures that any observed changes are due to changes in the reflectance of the diffuser panel, and not to changes in the calibration equipment.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

What is claimed is:

1. A method of measuring over time radiation from a subject on earth using an irradiance diffuser panel in space, the method comprising:

receiving, detecting, and comparing radiation from the subject and radiation from the panel to provide a measurement of radiation from the subject;

illuminating said panel with radiation incident upon said panel from a source of the radiation;

viewing said panel via a first port in a radiation averaging chamber to obtain a panel radiation intensity, said chamber including an integrating sphere;

sighting the source via a second port in said chamber to obtain a source radiation intensity;

comparing said panel radiation intensity to said source radiation intensity to obtain an initial value of a ratio of said panel radiation intensity to said source radiation intensity;

repeating said steps of viewing, sighting, and comparing over time to obtain successive values of said ratio of said panel radiation intensity to said source radiation intensity; and employing said successive values of said ratio to compensate said measurement of radiation from the subject for drifting in optical characteristics of said panel over time.

2. A method according to claim 1 wherein each of said viewing and said sighting steps includes a step of averaging said panel radiation intensity and said source radiation intensity, respectively, by said averaging chamber, said averaging chamber having a generally spherical shape and an interior diffuse reflecting surface.

3. A method according to claim 1 further comprising a step of baffling said first port to limit radiation entering said first port to radiation from said source as reflected by said panel to said first port.

4. A method according to claim 1 wherein said chamber has a first aperture and a second aperture located respectively at said first port and at said second port, said method further comprising substantially equalizing power of radiation entering said chamber via said first port and radiation entering said chamber via said second port by sizing said second aperture relative to said first aperture.

5. A method according to claim 1 further comprising steps of:

optically coupling a detector of radiation to said chamber via a third port of said chamber for detecting radiation within said chamber;

averaging radiation within said chamber by multiple internal reflections of radiation within said chamber; and wherein said viewing step provides for entry of radiation from said panel into said chamber;

said sighting step provides for entry of radiation from said source into said chamber; and said viewing and said sighting steps each include a detecting of radiation within said chamber by said detector.

6. A method according to claim 1 further comprising a step of enclosing said second port with a tubular structure to limit incoming radiation to said second port to radiation incident directly from the source to said second port.

7. A method according to claim 1 further comprising a step of shuttering said second port during said viewing step to exclude entry of radiation into said chamber via said second port during said viewing step.

8. A method according to claim 1 further comprising a step of shuttering said first port during said viewing step to exclude entry of radiation into said chamber via said first port during said viewing step.

9. Apparatus for measuring over time radiation from a subject on earth using an irradiance diffuser panel in space, the apparatus comprising:

means for receiving, detecting, and comparing radiation received from the subject and radiation from the panel to provide a measurement of radiation from the subject;

an averaging chamber including an integration sphere and having a first port and a second port and a third port for conducting radiation through a wall of the chamber, said first port serving to view radiation emanating from a source external to said chamber and reflected by said panel to said first port, said second port serving to sight radiation incident directly from the source upon said second port;

detector means optically coupled via said third port for detecting radiation within said chamber, said chamber having a diffuse internal reflecting surface to induce multiple diffuse reflections of radiation to average the radiation;

means coupled to said detector means for repeatedly comparing a value of radiation entering said chamber via said first port with a value of radiation entering said chamber via said second port to provide calibration values over time; and means for using said calibration values to compensate the measurement of radiation from the subject for drift in the characteristics of the panel over time.

10. Apparatus according to claim 9 wherein said comparing means includes means for dividing power of radiation entering said chamber via said first port by the power of radiation entering said chamber via said second port.

11. Apparatus according to claim 9 further comprising shutter means for excluding entry to said chamber of radiation via one of said ports during entry of radiation into said chamber via the other of said ports.

12. Apparatus according to claim 9 further comprising shutter means for excluding entry to said chamber of radiation via either of said ports, said shutter means including a first shutter located at said first port and a second shutter located at said second port, said shutter means further comprising means for activating said first shutter and said second shutter for passage of radiation in sequential fashion via said first port and said second port.

13. Apparatus according to claim 9 further comprising a baffle assembly encircling said first port to limit entry of radiation to said first port to radiation from the source as reflected by said panel to said first port.

14. Apparatus according to claim 9 further comprising a tubular structure encircling said second port for limiting radiation entering said second port to radiation incident directly from the source to said second port, the sun serving as the source, and said chamber being carried by a spacecraft.

15. Apparatus according to claim 9 wherein said detector means comprises a radiation detector and a fisheye lens located at said third port for gathering radiation from within said chamber for detection by said detector, said detector means further comprising an optical filter disposed between said lens and said detector for limiting a passage of radiation from said lens to said detector to radiation falling within a passband of said filter.

16. Apparatus according to claim 9 wherein said detector means comprises a plurality of radiation detectors and a plurality of optical filters disposed along paths of radiation incident upon respective ones of said detectors for limiting radiation to said detectors to radiation falling within passbands of respective ones of said filters.

17. Apparatus according to claim 16 wherein said detector means further comprises a plurality of fisheye lenses for gathering radiation from within said chamber for detection by respective ones of said detectors.

18. Apparatus according to claim 17 further comprising shutter means for excluding entry to said chamber of radiation via either of said ports, said shutter means including a first shutter located at said first port and a second shutter located at said second port, said shutter means further comprising means for activating said first shutter and said second shutter for passage of radiation in sequential fashion via said first port and said second port.

* * * * *